(12) United States Patent
Chabrol et al.

(10) Patent No.: US 10,718,684 B2
(45) Date of Patent: Jul. 21, 2020

(54) DEVICE FOR DETECTING A LEAK IN A SEALED ENCLOSURE

(71) Applicant: Commissariat à l'Energie Atomique et aux Energies Alternatives, Paris (FR)

(72) Inventors: Claude Chabrol, Poisat (FR); Jean-Yves Laurent, Domene (FR); Julien Routin, La Buisse (FR)

(73) Assignee: COMMISSARIAT À L'ENERGIE ATOMIQUE AUX ENERGIES ALTERNATIVES, Paris (FR)

( * ) Notice: Subject to any disclaimer, the term of this patent is extended or adjusted under 35 U.S.C. 154(b) by 239 days.

(21) Appl. No.: 16/063,262

(22) PCT Filed: Dec. 7, 2016

(86) PCT No.: PCT/FR2016/053257
§ 371 (c)(1),
(2) Date: Jun. 16, 2018

(87) PCT Pub. No.: WO2017/103382
PCT Pub. Date: Jun. 22, 2017

(65) Prior Publication Data
US 2018/0372577 A1    Dec. 27, 2018

(30) Foreign Application Priority Data
Dec. 17, 2015  (FR) ..................................... 15 62697

(51) Int. Cl.
*G01M 3/04*    (2006.01)
*A61N 5/06*    (2006.01)
*H01L 23/26*   (2006.01)

(52) U.S. Cl.
CPC .......... *G01M 3/047* (2013.01); *A61N 5/0601* (2013.01); *A61N 5/0622* (2013.01);
(Continued)

(58) Field of Classification Search
CPC .... G01N 2201/0628; G01N 2021/7783; H01L 23/26; H01L 2924/12044; H01L 27/3225
See application file for complete search history.

(56) References Cited

U.S. PATENT DOCUMENTS 3,943,557 A * 3/1976 Frazee ................. G01N 27/121
338/34
5,039,490 A * 8/1991 Marsoner ............. G01N 21/255
250/216

(Continued)

FOREIGN PATENT DOCUMENTS

AT         10020 U1 *  7/2008  ............. G01N 21/69
WO    2008082362 A1    7/2008
WO  WO-2008082362 A1 *  7/2008  ......... H01L 27/3225

OTHER PUBLICATIONS

Ghosh et al., "Thin-film encapsulation of organic light-emitting devices," Applied Physics Letters, vol. 86, No. 22, Jan. 1, 2005, 4 pages.

(Continued)

*Primary Examiner* — David A Rogers
(74) *Attorney, Agent, or Firm* — Moreno IP Law LLC

(57) ABSTRACT

The invention relates to a device for detecting a leak in a sealed enclosure, comprising an organic light-emitting diode intended to be placed inside the enclosure; and a device for measuring a value representative of at least one of the following parameters: a) the luminous efficacy of the diode; and b) the impedance of the diode.

8 Claims, 1 Drawing Sheet

(52) U.S. Cl.
CPC ............... *A61N 2005/0653* (2013.01); *G01N 2201/0628* (2013.01); *H01L 23/26* (2013.01)

(56) References Cited

U.S. PATENT DOCUMENTS

| | | | | |
|---|---|---|---|---|
| 6,045,756 | A * | 4/2000 | Carr | G01N 21/7703 422/534 |
| 6,331,438 | B1 * | 12/2001 | Aylott | G01N 21/66 422/82.07 |
| 6,818,479 | B2 * | 11/2004 | Boroson | H01L 23/08 257/678 |
| 6,998,776 | B2 * | 2/2006 | Aitken | C03C 3/072 313/512 |
| 7,091,605 | B2 * | 8/2006 | Boroson | H01L 23/08 257/433 |
| 7,723,711 | B2 * | 5/2010 | Schoo | G01N 21/274 250/576 |
| 7,947,111 | B2 * | 5/2011 | Torres, Jr. | B01J 20/06 257/682 |
| 8,233,953 | B2 * | 7/2012 | Colvin, Jr. | G01N 21/552 600/316 |
| 8,915,121 | B2 * | 12/2014 | Kumar | B82Y 20/00 73/29.01 |
| 9,372,165 | B2 * | 6/2016 | Lee | G01N 27/126 |
| 9,651,482 | B2 * | 5/2017 | Blei | G01N 21/4738 |
| 2002/0016535 | A1 * | 2/2002 | Martin | A61B 5/0031 600/319 |
| 2003/0140931 | A1 * | 7/2003 | Zeijlemaker | A61N 1/365 128/899 |
| 2004/0181155 | A1 * | 9/2004 | Glukhovsky | A61B 1/00147 600/476 |
| 2004/0199059 | A1 * | 10/2004 | Brauker | A61B 5/14532 600/309 |
| 2005/0184661 | A1 * | 8/2005 | Chiu | G01N 27/121 313/512 |
| 2006/0067645 | A1 * | 3/2006 | Gally | B81C 99/0045 385/147 |
| 2013/0194199 | A1 | 8/2013 | Lynch et al. | |

OTHER PUBLICATIONS

Smith et al., "Application of flexible OLED Display Technology for Electro-Optical Stimulation and/or Silencing of Neural Activity," Journal of Display Technology, vol. 10, No. 6, Jun. 1, 2014, 8 pages.
International Search Report for PCT/FR2016/053257 dated Mar. 7, 2017, 3 pages.
Written Opinion of the International Searching Authority for International Application No. PCT/FR2016/053257, dated Mar. 7, 2017, 7 pages.

* cited by examiner

DEVICE FOR DETECTING A LEAK IN A SEALED ENCLOSURE

FIELD

The present application relates to a device for detecting a leak in a sealed enclosure. The present application particularly relates to the detection of a leak in a sealed enclosure intended to be implanted in the human or animal body.

BACKGROUND

There is a growing need for electronic devices implantable in the human or animal body, for example, to implement electric or optical stimulations of internal organs of the human or animal body. Such devices may particularly comprise electronic circuits integrating non-biocompatible materials. In this case, the device may comprise a biocompatible enclosure or package hermetically encapsulating the non-biocompatible components. The hermeticity of the package particularly enables to avoid for physiologic fluid to come into contact with the non-biocompatible components of the device, which might cause an intoxication of the patient. The hermeticity of the package further enables to limit risks of corrosion of the device components.

To improve the patient's security, it would be desirable to be able to detect in-situ, that is, without having to remove the device from the patient's body, a possible leak in a sealed enclosure of an implantable medical device.

Various methods have been provided to detect a leak in a sealed package. Such methods are however relatively complex and, for some of them, can only be implemented outside of the patient's body. Further, known methods are poorly adapted to the detection of leaks in small enclosures, for example, having a volume smaller than 10 mm$^3$, which may be encountered in the field of implantable medical devices.

SUMMARY

Thus, an embodiment provides a device for detecting a leak in a sealed enclosure, including an organic light-emitting diode intended to be placed within the enclosure; and a device for measuring a quantity representative of at least one of the following parameters: a) the luminous efficiency of the diode; and b) the impedance of the diode.

According to an embodiment, the device further comprises a processing circuit capable of comparing said quantity to one or a plurality of reference values, and of deducing therefrom the possible presence of oxygen or of humidity by abnormal proportions within the enclosure.

According to an embodiment, the processing circuit is capable of controlling an alarm.

According to an embodiment, the measurement device comprises a photodetector placed opposite the organic light-emitting diode.

According to an embodiment, the photodetector is made up of an inorganic semiconductor material.

Another embodiment provides a medical device comprising a sealed biocompatible enclosure, and a device for detecting a leak in the sealed enclosure such as defined hereabove.

According to an embodiment, the sealed enclosure is transparent and contains a source of optical stimulation of the brain.

According to an embodiment, the sealed enclosure comprises a transparent tube.

According to an embodiment, the tube is hermetically closed at its ends by caps.

According to an embodiment, the device comprises electric connection elements crossing at least one of the caps and electrically coupling to the outside of the enclosure components located within the tube.

BRIEF DESCRIPTION OF THE DRAWINGS

The foregoing and other features and advantages will be discussed in detail in the following non-limiting description of specific embodiments in connection with the accompanying drawings, among which.

DETAILED DESCRIPTION OF THE PRESENT EMBODIMENTS

Figure 1:
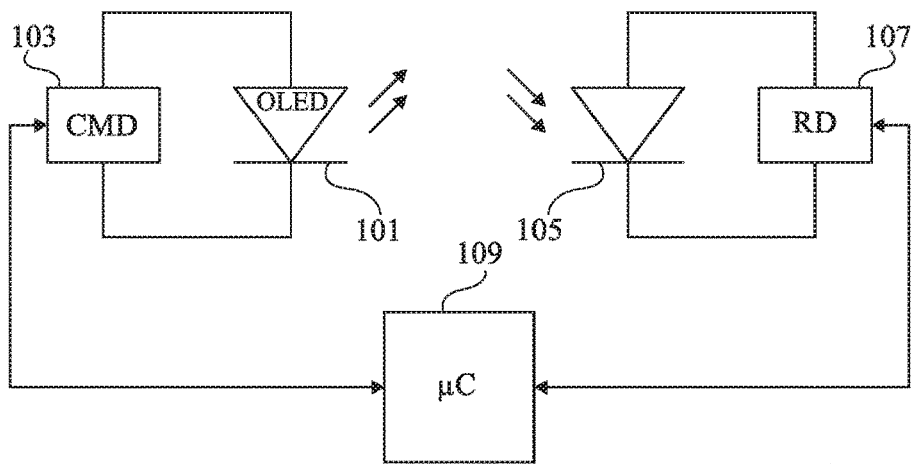
FIG. 1 schematically shows an embodiment of a device for detecting the presence of a leak in a sealed enclosure.

The same elements have been designated with the same reference numerals in the different drawings and, further, the various drawings are not to scale. For clarity, only those elements which are useful to the understanding of the described embodiments have been shown and are detailed. In particular, the various components (other than the components of the leak detection device) capable of being deposited in a sealed biocompatible package for an implantation in a patient's body have not been shown and are not detailed, the described embodiments being compatible with all known implantable device comprising a sealed encapsulation package. The terms "approximately", "substantially", and "in the order of" are used herein to designate a tolerance of plus or minus 10%, preferably of plus or minus 5%, of the value in question.

According to an aspect of an embodiment, it is provided to use an organic light-emitting diode (OLED) arranged within a sealed enclosure to detect the possible presence of a leak in this enclosure.

Organic light-emitting diodes (OLEDs) are indeed known to have a degraded performance in the presence of humidity or of oxygen. In particular, in the presence of humidity or of oxygen, the luminous efficiency of an organic light-emitting diode decreases rapidly and its impedance increases rapidly.

According to an aspect of an embodiment, it is provided to take advantage of this known defect of organic light-emitting diodes to detect a presence of humidity or oxygen by abnormal proportions in a sealed enclosure, and to deduce therefrom the possible presence of a leak in the enclosure.

FIG. 1 is a simplified representation of an embodiment of a device for detecting a leak in a sealed enclosure (not shown).

The device of FIG. 1 comprises an organic light-emitting diode 101 (OLED) intended to be placed inside of the sealed enclosure. Diode 101 comprises at least one layer made of an organic semiconductor material arranged between an anode electrode and a cathode electrode of the diode. When an adapted current is applied between the anode and the cathode of diode 101, photons are generated by the organic semiconductor layer and diode 101 emits light. It should be noted that there exist many organic light-emitting diode manufacturing technologies, based on the use of different organic semiconductor materials, and/or on different layouts of these materials. However, all known organic light-emitting diodes have as a common point a high sensitivity to humidity and/or to oxygen. Thus, the described embodiments may be implemented whatever the type of organic light-emitting diode 101 used.

The device of FIG. 1 further comprises a unit or circuit 103 for powering and controlling (CMD) diode 101, connected to the anode and to the cathode of diode 101. Unit 103 for example comprises an electric battery or any other adapted power source, as well as a circuit enabling to control diode 101 to the on or off state.

The device of FIG. 1 further comprises a photodetector 105 arranged opposite diode 101, capable of supplying an electric signal representative of the light intensity emitted by diode 101. Photodetector 105 is for example a photodiode. Photodetector 105 may be made up of an inorganic semiconductor material, for example, silicon.

The device of FIG. 1 further comprises a unit or circuit 107 for reading (RD) an electric quantity representative of the illumination level received by photodetector 105.

Further, the device of FIG. 1 comprises a processing circuit 109 (µC), for example comprising a microprocessor, where this circuit is coupled to readout unit 107 and may further be coupled to power supply and control unit 103.

The device of FIG. 1 operates as follows. In a detection phase, device 103 orders the turning on of diode 101. For this purpose, device 103 for example applies to diode 101 a predetermined fixed power supply voltage or a predetermined fixed power supply current or a predetermined fixed power (current*voltage). When diode 101 is on, the assembly formed by photodetector 105 and readout unit 107 measures a quantity representative of the light intensity emitted by diode 101. Based on this measurement and knowing the electric power supplied to diode 101, processing circuit 109 can estimate the luminous efficiency of diode 101. Processing circuit 109 compares the measured efficiency to one or a plurality of reference values and can thus detect an abnormal decrease of the luminous efficiency of diode 101 a deduce therefrom the presence of humidity or of oxygen by abnormal proportions within the enclosure. In particular, if the luminous efficiency of diode 101 is smaller than expected, processing circuit 109 can deduce therefrom that the oxygen rate and/or the humidity rate within the enclosure is abnormally high, which has resulted in prematurely degrading the diode efficiency. Processing circuit 109 may in particular deduce therefrom the presence of a leak in the sealed enclosure containing diode 101. When processing circuit 109 detects a leak in the enclosure, it for example triggers an alarm to notify this leak.

To determine the reference luminous efficiency values used by processing circuit 109 to detect the possible presence of a leak in the enclosure, a phase of characterization of photodiode 101 may be provided on design of the device. In particular, the time variation of the luminous efficiency of diode 101 may be determined on the one hand for a normal use of the device, that is, in the absence of a leak in the sealed enclosure containing diode 101, and in the other hand in the occurrence of a leak. The laws of variation of the luminous efficiency determined during the characterization phase may be stored in processing circuit 109, for example, in the form of tables.

Figure 2:
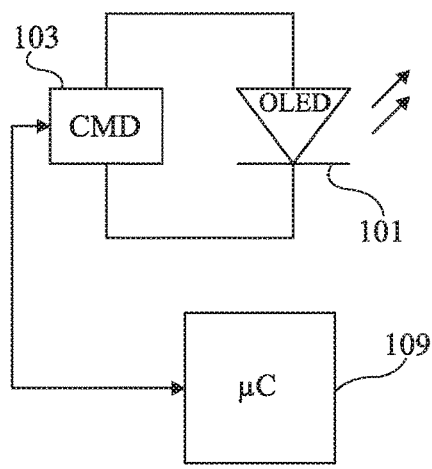
FIG. 2 schematically shows an alternative embodiment of the device of FIG. 1.

FIG. 2 is a simplified representation of an alternative embodiment of the leak detection circuit of FIG. 1.

The device of FIG. 2 differs from the device of FIG. 1 mainly in that it does not comprise photodetector 105 and readout unit 107 of the device of FIG. 1.

In the device of FIG. 2, unit 103 for powering and controlling (CMD) diode 101 is capable of measuring the impedance of diode 101. To achieve this, unit 103 is for example capable of applying a predetermined voltage between the anode and the cathode of diode 101, and of measuring the current flowing through diode 101 while this diode is applied. As a variation, unit 103 is capable of applying a predetermined current between the anode and the cathode of diode 101, and of measuring the voltage across diode 101 while this current is applied. Unit 103 for powering and controlling diode 101 is capable of communicating to processing circuit 109 the measured impedance values.

The device of FIG. 2 operates as follows. During a detection phase, device 103 measures the impedance of diode 101, for example, in the on state (that is, the voltage and the current applied to diode 101 during the impedance measurement are capable of causing the turning on of diode 101). Circuit 109 compares the measured impedance value with one or a plurality of reference values, and thus detects an abnormal increase of the impedance of diode 101, and deduces therefrom the presence of humidity or of oxygen by abnormal proportions within the enclosure. Processing circuit 109 may in particular deduce therefrom the presence of a leak in the sealed enclosure containing diode 101 and, if need be, trigger an alarm to notify this leak.

To determine the reference impedance values used by circuit 109 to detect the possible presence of a leak in the enclosure, a phase of characterization of photodiode 101 may be provided on design of the device. In particular, the time variation of the impedance of diode 101 may be determined, on the one hand, for a normal use of the device, that is, in the absence of a leak in the sealed enclosure containing diode 101, and, on the other hand, in the occurrence of a leak. The impedance variation laws determined during the characterization phase may be stored in processing circuit 109, for example, in the form of tables.

It should be noted that the alternative embodiments described in relation with FIGS. 1 and 2 may be combined, that is, the leak detection device may use both measurements representative of the luminous efficiency of diode 101 and measurements representative of the impedance of diode 101 to detect a possible variation of the humidity rate or of the oxygen rate in the sealed enclosure containing diode 101, and to deduce therefrom the presence of a leak in this enclosure.

Figure 3:
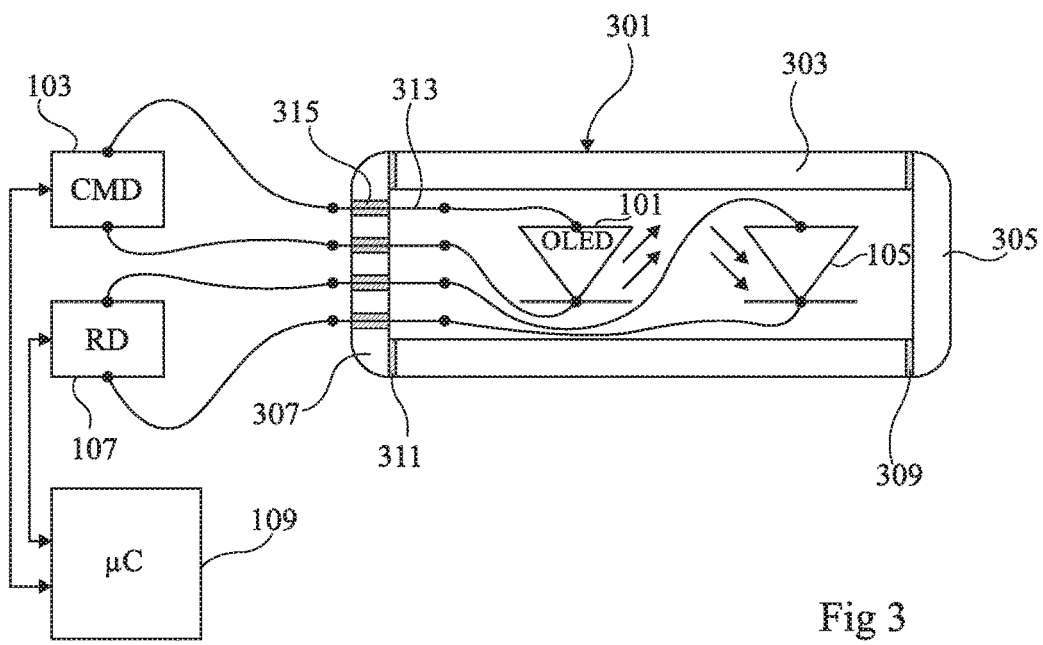
FIG. 3 schematically shows an embodiment of a medical device comprising a sealed biocompatible enclosure and a device for detecting the presence of a leak in this enclosure.

FIG. 3 is a cross-section view schematically and partially showing an embodiment of a medical device comprising a sealed implantable biocompatible enclosure 301 and a device of the type described in relation with FIGS. 1 and 2 enabling to detect the possible presence of a leak in enclosure 301.

The device of FIG. 3 is a device of optical stimulation of internal organs of the human or animal body, for example, an optical deep brain stimulation device. Enclosure 301 contains a stimulation light source (not shown) and is intended to be implanted inside of the brain, opposite a portion of the brain which is desired to be stimulated.

Enclosure 301 comprises a tube 303 made of a transparent biocompatible material, for example, sapphire or silica, having the stimulation light source arranged therein. Tube 303 for example has a circular cross-section. As an example, the width of tube 303 (that is, its diameter in the case of a tube having a circular cross-section) is in the range from 0.5 to 5 mm, and its length is in the range from 1 to 10 mm. Enclosure 301 further comprises caps 305 and 307 hermetically closing tube 303 at its ends. Caps 305 and 307 are for example transparent. As an example, caps 305 and 307 are made of the same transparent biocompatible material as tube 303. Cap 305 is welded all along its periphery to a first end of tube 303 by a sealed biocompatible welding 309, for example, a gold solder. Cap 307 is soldered all along its periphery to a first end of tube 303 by a sealed biocompatible solder 311, for example, a gold solder. The fastening of caps 305 and 307 to the ends of tube 303 is for example performed by thermosonic welding or by thermocompression. Once caps 305 and 307 are in place, the assembly comprising tube 303 and caps 305 and 307 forms a sealed package capable of isolating all the non-biocompatible components that it contains, for example, a package having a helium leakage rate smaller than 10-6 atm·cm3/s, preferably smaller than 10-8 atm·cm3/s, with 1 atm=101,325 Pa. As an example, package 109 is closed under a neutral atmosphere (oxygen-free), for example, under nitrogen or argon.

The device of FIG. 3 further comprises a leak detection device of the type described in relation with FIG. 1. Organic light-emitting diode 101 of the leak detection device is arranged within enclosure 301. Photodetector 105 of the leak detection device is also arranged within the enclosure, opposite diode 101. In this example, unit 103 for powering and controlling diode 101, unit 107 for reading from photodetector 105 and processing circuit 109 of the leak detection device are arranged within enclosure 301. As an example, elements 103, 107, and 109 may be arranged outside of the patient's body or be implanted in another portion of the patient's body (outside of the brain).

In the shown example, electric connection elements 313 crossing enclosure 301 electrically couple to the outside of the enclosure the components located within the enclosure, and in particular diode 101 and photodetector 105. In the shown example, each electric connection element 313 comprises a conductive rod thoroughly crossing cap 307 via a hole or via pierced in the cap. Each of the vias is hermetically closed by a solder 315, for example, a gold solder. A connecting cable may be provided to electrically couple electric connection elements 313 to units 103 and 107.

More generally, the described leak detection devices may equip any type of sealed biocompatible package (transparent or not) intended to be implanted in a patient's body.

An advantage of the described leak detection devices is that they are particularly simple to implement. Further, such devices are capable of detecting leaks in small enclosures. It should further be noted that organic light-emitting diode 101 may be used not only to monitor the hermeticity of the enclosure containing it, but also for other functions, for example as a light emitter for the optical irradiation of the patient's brain in the case of an optical stimulation device of the type described in relation with FIG. 3.

Specific embodiments have been described. Various alterations and modifications will occur to those skilled in the art. In particular, the described embodiments are not limited to leak detection in sealed implantable biocompatible packages, but may more generally have other applications, particularly outside of the medical field.

What is claimed is:

1. A device for detecting a leak in a sealed enclosure, comprising:
    an organic light-emitting diode intended to be placed within the enclosure;
    a device for measuring a quantity representative of at least one of the following parameters:
    a) the luminous efficiency of the diode; and
    b) the impedance of the diode; and
    a processing circuit capable of comparing said quantity to one or a plurality of reference values, and of deducing therefrom the possible presence of oxygen or humidity by abnormal proportions within the enclosure,
    wherein the processing circuit is capable of controlling an alarm when it detects a presence of oxygen or of humidity by abnormal proportions within the enclosure.

2. The detection device of claim 1, wherein the measurement device comprises a photodetector arranged opposite the organic light-emitting diode.

3. The device of claim 2, wherein the photodetector is made up of an inorganic semiconductor material.

4. A medical device comprising a sealed biocompatible enclosure and the device of claim 1 for detecting a leak in the sealed enclosure.

5. The medical device of claim 4, wherein the sealed enclosure is transparent, and contains a source of optical stimulation of the brain.

6. The medical device of claim 5, wherein the sealed enclosure comprises a transparent tube.

7. The medical device of claim 6, wherein the tube is hermetically closed at its ends by caps.

8. The device of claim 7, comprising electric connection elements crossing at least one of the caps and electrically coupling to the outside of the enclosure components located inside of the tube.

* * * * *